(12) United States Patent
Loubens et al.

(10) Patent No.: US 6,197,035 B1
(45) Date of Patent: Mar. 6, 2001

(54) APPLICATOR FOR SETTING A SURGICAL NEEDLE

(75) Inventors: Thierry Loubens; Lionel Riou; ANtoine Watrelot, all of Lyons (FR)

(73) Assignee: Soprane SA, Lyons (FR)

( * ) Notice: Subject to any disclaimer, the term of this patent is extended or adjusted under 35 U.S.C. 154(b) by 0 days.

(21) Appl. No.: 09/445,452

(22) PCT Filed: Jun. 16, 1998

(86) PCT No.: PCT/FR98/01263

§ 371 Date: Feb. 3, 2000

§ 102(e) Date: Feb. 3, 2000

(87) PCT Pub. No.: WO98/57584

PCT Pub. Date: Dec. 23, 1998

(30) Foreign Application Priority Data

Jun. 16, 1997 (FR) .................................................. 97/07681

(51) Int. Cl.$^7$ .................................................. A61B 17/04
(52) U.S. Cl. .......................... 606/139; 606/144; 606/148
(58) Field of Search .................................. 606/139, 144, 606/147, 148, 219, 222, 1

(56) References Cited

U.S. PATENT DOCUMENTS

| | | | | |
|---|---|---|---|---|
| 2,738,790 | * | 3/1956 | Todt, Sr. et al. ...................... | 606/148 |
| 4,602,635 | * | 7/1986 | Mulhollan et al. ................... | 606/148 |
| 4,784,139 | * | 11/1988 | Demos ................................. | 606/148 |
| 4,841,888 | * | 6/1989 | Mills et al. .......................... | 112/169 |
| 4,923,461 | * | 5/1990 | Caspri et al. ........................ | 606/148 |
| 4,926,860 | * | 5/1990 | Stice et al. .......................... | 606/144 |
| 4,935,027 | * | 6/1990 | Yoon .................................... | 606/148 |
| 4,968,315 | * | 11/1990 | Gatturna ............................... | 606/139 |
| 5,037,433 | | 8/1991 | Wilk et al. ........................... | 606/139 |
| 5,059,201 | * | 10/1991 | Asnis ................................... | 606/144 |
| 5,090,419 | * | 2/1992 | Palestrant ............................ | 128/754 |
| 5,176,691 | | 1/1993 | Pierce ................................... | 606/148 |
| 5,281,237 | | 1/1994 | Gimpelson ........................... | 606/144 |

FOREIGN PATENT DOCUMENTS

| | | |
|---|---|---|
| 529675 | 8/1992 | (EP) . |
| 92/05828 | 4/1992 | (WO) . |

* cited by examiner

*Primary Examiner*—Gary Jackson
(74) *Attorney, Agent, or Firm*—Greenblum & Bernstein, P.L.C.

(57) ABSTRACT

An applicator for setting a needle secured to a suture thread, a method of assembling the applicator and a method of using the applicator. The applicator includes an elongated sleeve comprising a bore, a first end and a second end, the needle being disposed within the bore near the second end, a rod having a first end and a second end, the second end being adapted to slide within the bore and rest adjacent the needle, and a retaining mechanism for maintaining the position of the rod with respect to the elongated sleeve. The method of assembling includes securing the suture thread to the needle, placing the needle and a portion of the thread into the bore of the elongated sleeve, introducing the second end of the rod into the bore until it is positioned adjacent the needle, retaining the first end of the rod on the retaining mechanism, and retaining the first end of the elongated sleeve on the retaining mechanism. The method of using includes releasing the first end of the rod from the retaining mechanism, releasing the first end of the elongated sleeve from the retaining mechanism, and moving the first end of the rod towards the first end of the elongated sleeve, wherein the second end of the rod forces the needle out of the second end of the elongated sleeve when the rod is moved.

31 Claims, 9 Drawing Sheets

APPLICATOR FOR SETTING A SURGICAL NEEDLE

BACKGROUND OF THE INVENTION

FIELD OF THE INVENTION

The present invention relates to an applicator for setting a needle secured to its suture thread in place in a surgical site.

SUMMARY OF THE INVENTION

The applicator according to the present invention is also intended for endoscopy procedures so that it can collaborate, for example, with a small-diameter trocar to convey the needle to the surgical site and release it there.

The applicator according to the invention comprises a sleeve in which a needle is held in an approximately elongate position, a rod which enters the sleeve to extract the needle and retaining mechanism which, before the needle is extracted, allow the rod to be held inside the sleeve in a position that is determined such that the free end of the rod rests against the needle.

The applicator according to the present invention, in the internal part of the sleeve, comprises tensioning mechanism which allow the suture thread to be kept taut while the needle is being extracted.

BRIEF DESCRIPTION OF THE DRAWINGS

The description which will follow with reference to the appended drawings, which are given merely by way of nonlimiting example, will allow a better understanding of the invention, the features it has and the advantages it is likely to afford.

FIGS. 1 to 4 depict an applicator 1 for setting a needle 2 secured to a suture thread 9 in place in the surgical site using a trocar 3 which has already been inserted through the wall 4 of a patient.

DETAILED DESCRIPTION OF THE INVENTION

Figure 1:
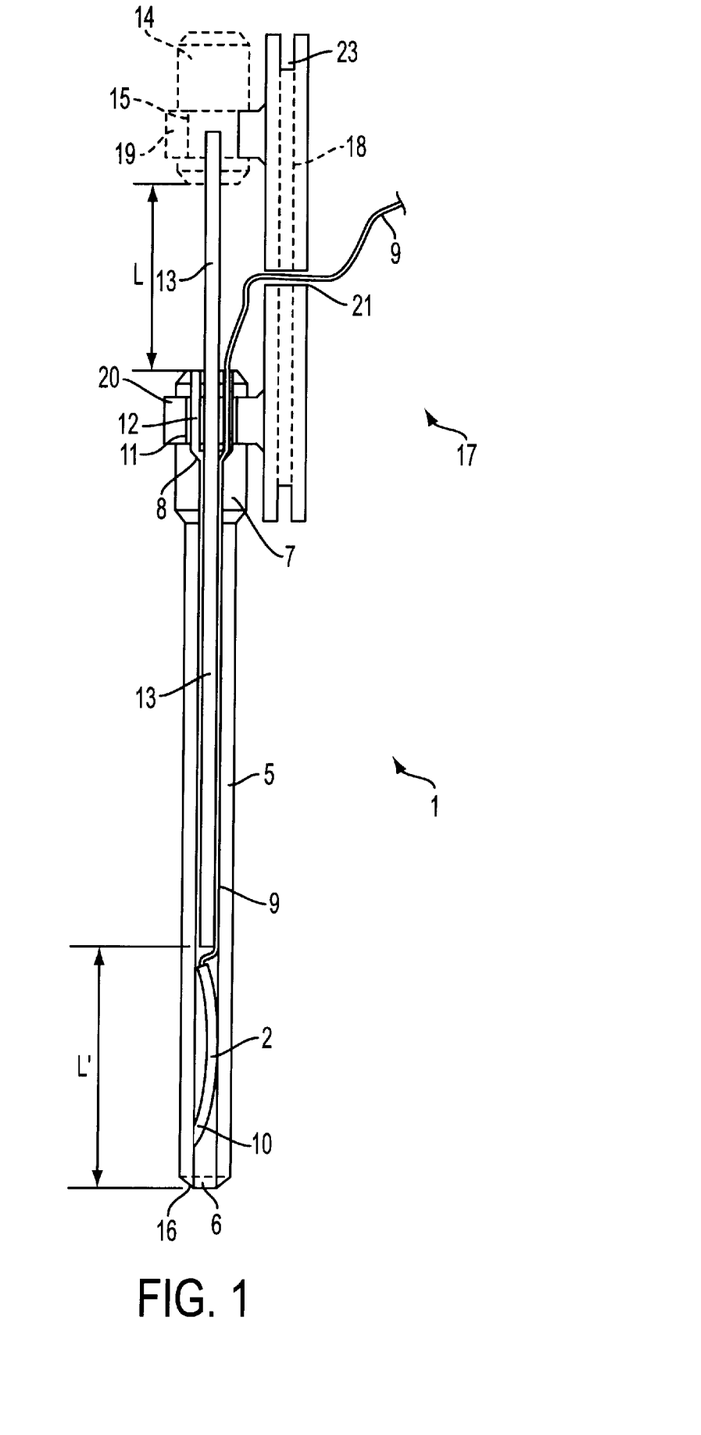
FIG. 1 is a section illustrating the applicator for setting a needle in place according to the present invention.

The applicator 1 comprises a cylindrical sleeve 5 pierced along its entire length and parallel to its longitudinal axis with a bore 6 in which the needle 2 and its suture thread 9 are housed.

The sleeve 5, at one of its ends, has a cylindrical head 7 which is designed to have a diameter that exceeds that of the rest of the body of the sleeve. Pierced inside the head 7, coaxial with the bore 6, is a housing 8 which has a larger diameter than the bore.

The housing 8 communicates with the bore 6 in such a way that the suture thread 9 secured to the needle 2 can pass out toward the outside of the sleeve 5. Specifically, the needle 2 is arranged inside the bore 6 of the sleeve 5 in such a way that its pointed end 10 faces toward the free end 16 and away from the end bearing the head 7.

Note that the pointed end 10 of the needle 2 is set back slightly from the free end 16 of the sleeve 5.

The head 7 of the sleeve 5, on its external face, has a circular recess 11, the function of which will become clearer later on.

A flexible ring 12 which constitutes a mechanism for tensioning the suture thread 9 inside the bore 6 of the sleeve S is introduced coaxially into the housing 8. What happens is that the ring 12 slightly wedges the suture thread 9 against the internal wall of the housing 8. Under these conditions, it can be seen that the suture thread 9 is arranged between the external face of the ring 12 and the internal wall of the housing 8.

The needle 2 is retained slightly, because of its elastic deformation, inside the bore 6 of the sleeve 5, making it possible, when the suture thread 9 is pulled, to tension it between the needle and the ring 12 inside the bore 6.

Note that the pointed end 10 of the needle 2 is set back slightly from the free end of the sleeve 5 which is at the opposite end from the head 7.

The applicator 1 comprises a rod 13 which is secured at one of its ends to a cylindrical stop 14 which, on its external face, has a circular recess 15, the function of which will become clearer later on.

The rod 13 is introduced into the sleeve 5 in such a way that it comes to rest against the needle 2. The rod 13 passes through the ring 12 and the bore 6 in such a way that the suture thread 9 is arranged between the rod 13 and the wall of the bore 6.

Retaining mechanism 17 allows the rod 13 to be held with respect to the sleeve 5 in such a way that the free end of the rod 13, which is the opposite end to the stop 14, always rests against the needle 2.

Figure 2:
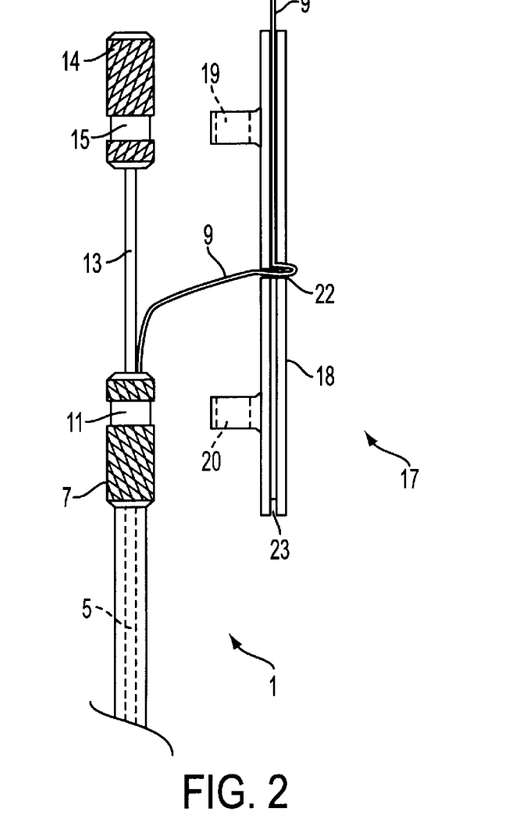
FIGS. 2 and 3 are side views showing the applicator prior to the fitting of the mechanism of retaining the rod with respect to the sleeve.
Figure 3:
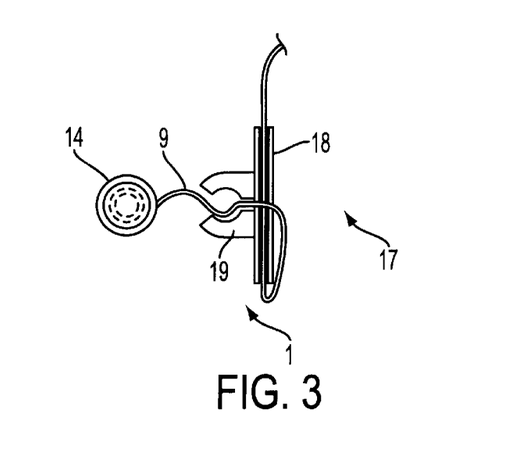

The retaining mechanism 17 utilizes in a plate 18 secured on one of its faces to two grippers 19 and 20 which are elastically deformed to form two fastening clips. One of the grippers 19 and 20 collaborates with the recess 15 of the stop 14 secured to the rod 13 and the other one collaborates with the recess 11 of the head 7 of the sleeve 5.

The position of the two grippers 19 and 20 on the plate 18 makes it possible to maintain a constant distance L between the stop 14 of the rod 13 and the head 7 of the sleeve 5. This distance L ensures that the free end of the rod 13, that is to say the opposite end to the stop 14, is, on the one hand, in contact with the needle 2 and, on the other hand, a distance L', identical to the distance L, away from the free end 16 of the sleeve 5.

Figure 4:
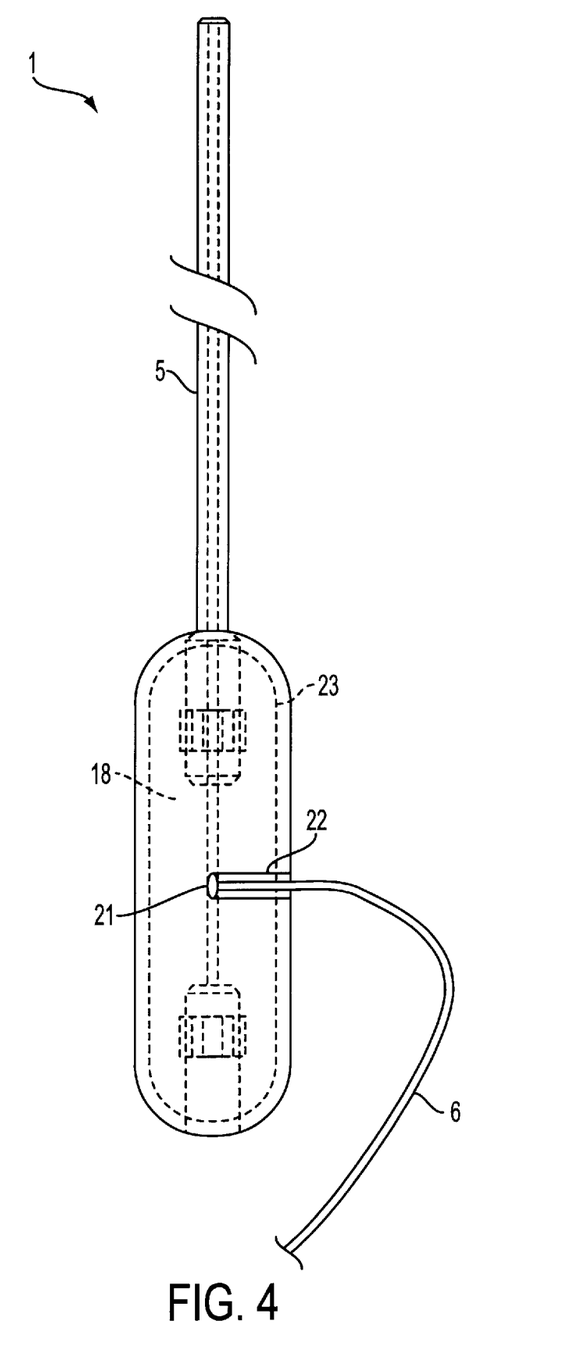
FIG. 4 is a view from above depicting the applicator according to the present invention.

The plate 18 also utilizes a reel onto which the thread 9 on the outside of the applicator 1 can be wound.

The plate 18 has an elongate, approximately oblong shape pierced at its middle with an emergent hole 21.

The hole 21 communicates via a slit 22 with a groove 23 which is formed along the entire periphery of the plate 18. The slit 22 is on the opposite face to the face which bears the grippers 19 and 20.

That part of the suture thread 9 which is on the outside of the sleeve 5 passes through the central hole 21 to enter the peripheral groove 23 via the slit 22 and be wound up in the groove 23. The free end of the thread 9 may, for example, be wedged in the groove 23 using a small plug of silicone, not depicted, allowing the suture thread to be held on the plate 18.

Preparation of the applicator 1 in a clean room or sterile area provides for in:

Introducing a needle 2, capable of elastic deformation or having similar properties and which is secured to a suture thread 9, into the bore 6 of the sleeve 5 in such a way that its pointed end 10 points toward the free end 16, Arranging the retaining ring 12 in the housing 8 of the sleeve 5 to slightly wedge the suture thread 9 between the ring and the wall of the housing, Pulling gently on the suture thread 9 to make it taut inside the bore 6 of the sleeve 5, Introducing the rod 13 into the bore 6 of the sleeve 5 to place the suture thread 9 between the rod 13 and the internal wall of the bore 6, Immobilizing the rod 13 with respect to the sleeve 5 using the plate 18 so that the stop 14 is a distance L away from the head 7, ensuring that the end of the rod 13 is in contact with the needle 2, Winding the suture thread 9 around the plate 18, Fixing the suture thread onto the plate 18, Placing the applicator 1 equipped with the needle 2 in a sterile bag.

Figure 5:
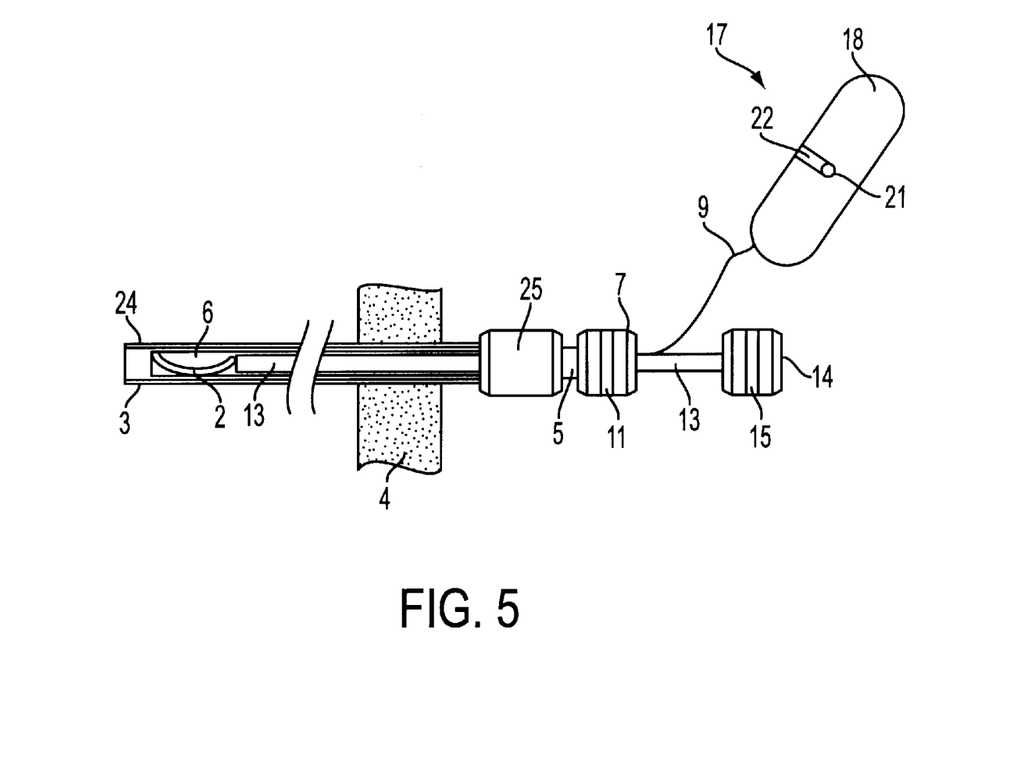
FIG. 5 is a diagrammatic view of the applicator according to the present invention in a trocar prior to the release of the needle.

FIG. 5 shows the applicator 1 arranged inside the trocar 3 which has already been placed through the wall 4 of a patient.

The trocar consists of a tube 24 secured at one of its ends to a circular skirt 25 which acts as a rest for the applicator when the needle 2 is being set in place at the surgical site, as will be seen better later.

The tube 24 of the trocar 3 is designed to take the sleeve 5 of the applicator 1, while the head 7 comes to rest against the circular skirt 25.

The surgeon then withdraws the retaining mechanism 17 and more specifically the plate 18 to release the rod 13 from the sleeve 5.

Note that the part of the suture thread 9 which is on the outside of the applicator 1 can remain wound around the reel or plate 18 during the operation of introducing the needle 2 into the surgical site.

Figure 6:
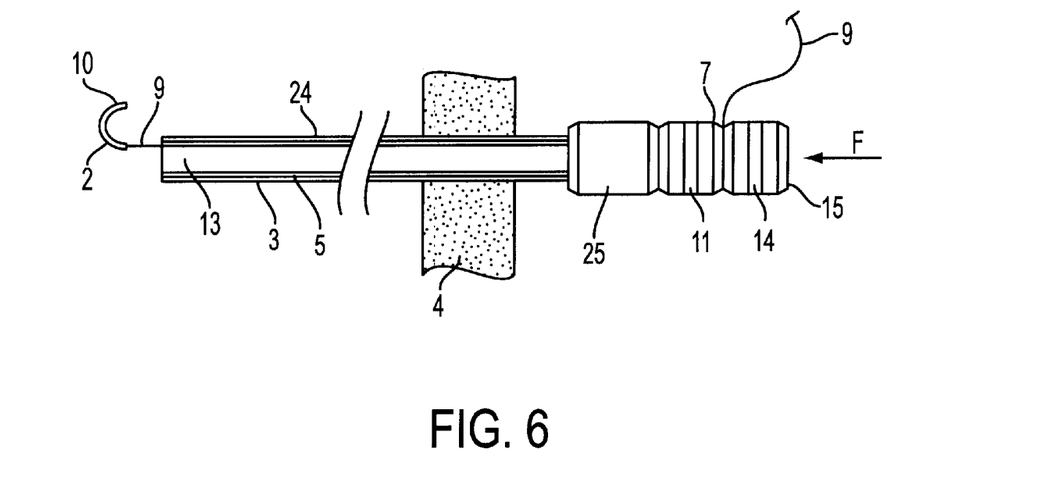
FIG. 6 is a view similar to that of FIG. 5 but showing the needle at the surgical site.

FIG. 6 shows the extraction of the needle 2 from the sleeve 5 of the applicator 1.

Specifically, all the surgeon needs to do is press, in the direction of the arrow F, on the stop 14 of the rod 13 so as, via the rod 13, to push the needle 2 out of the sleeve 5. The movement of the rod 13 is limited in its travel until such point as the stop 14 comes into contact with the head 7 of the sleeve 5.

It will be noted that the movement of the stop 14 by a distance L guarantees that the free end of the rod 13 is moved by an identical distance L' and that the needle 2 has been extracted from the sleeve 5.

Furthermore, the tensioning mechanism arranged inside the head 7 and utilizing the ring 12 allows the suture thread 9 to remain taut inside the bore 6 during the extraction of the needle 2 so as to avoid any possibility of this suture thread becoming bunched up inside the sleeve 5 and around the rod 13.

Note that, on account of its elasticity, the needle 2 reverts to its arc shape.

Furthermore, the needle 2 is retained by use of its suture thread 9 near the trocar 3 by way of the suture thread 9, which is either slightly wedged by the ring 12 or at the same time held by the ring 12 and the plate 18.

Next, the surgeon recovers the needle 2 using grippers, not depicted, at the same time withdrawing the rod 13 from the sleeve 5.

Prior to recovering the needle 2 from the surgical site, the suture thread is completely unwound from the reel to allow the surgeon to perform his task.

To make the sleeve 5 easier to grasp, it is possible to add, around the head 7, a mechanism not depicted, for immobilizing the surgeon's fingers so that the surgeon can use the applicator in just one hand in the manner of a syringe.

Figure 7:
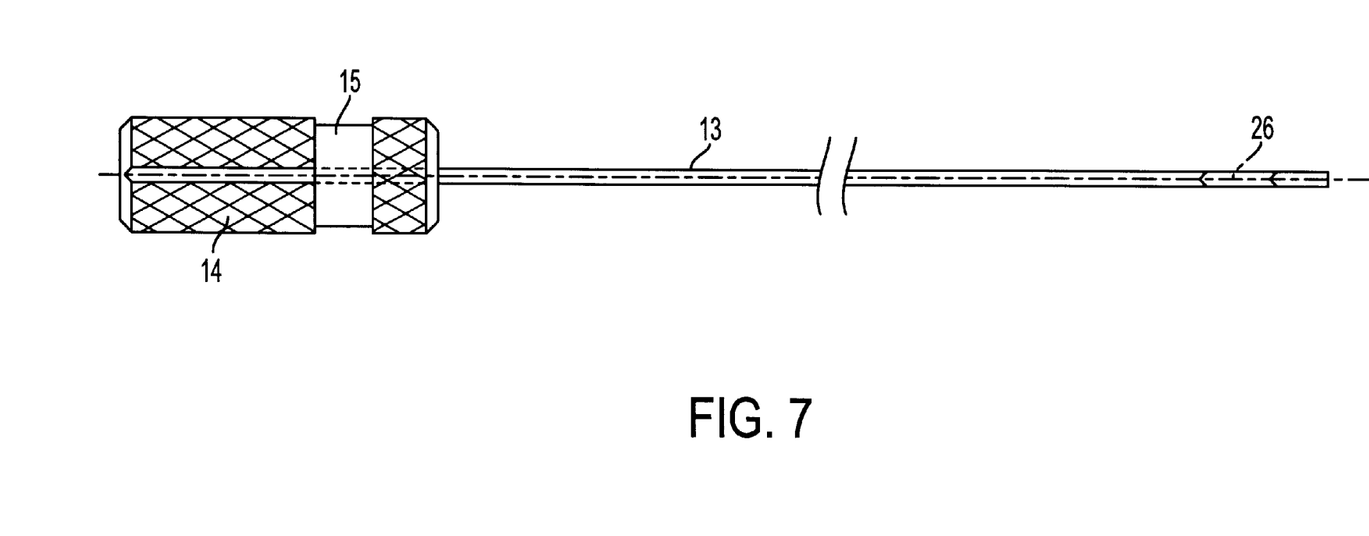
FIGS. 7 and 8 are views illustrating an alternative form of the rod coming to rest against the needle held in the applicator.
Figure 8:
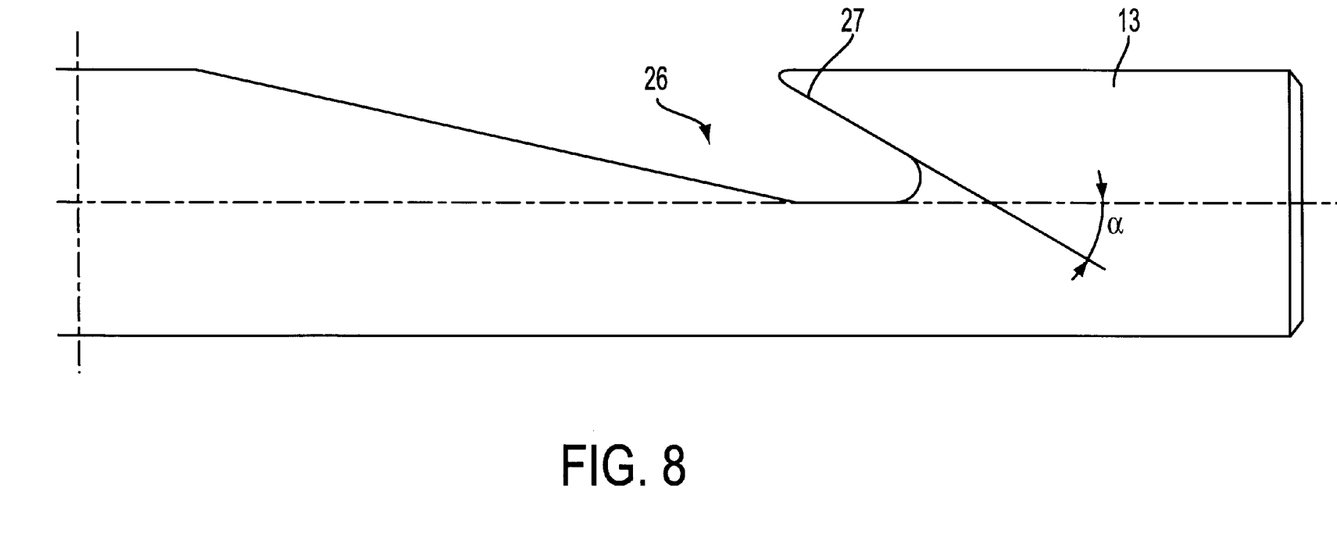

FIGS. 7 and 8 depict an alternative form of the rod 13 introduced into the applicator 1 according to the present invention.

At its free end, which is the opposite end to the cylindrical stop 14, the rod 13 has a hook-shaped notch 26 facing toward said stop. The notch 26 formed in the thickness of the rod 13 has a surface 27 which is inclined by an angle a of about 30 degrees.

The inclination of the surface 27 delimits the opening of the notch 26. Note that the depth of the notch 26 does not go beyond the central and longitudinal axis of the rod 13.

The modified rod 13 makes it possible, on the one hand, to carry out the same function described earlier in order to introduce the needle 2 to the operating site and, on the other hand, to use the hook 26 to recover the suture thread 9 at the middle of the operating site and lead it out of the human body, leaving the needle inside so that extra-corporal knots can be tied.

The suture thread 9 is extracted either through the applicator 1 or through the trocar 3, depending on the surgeon's requirements.

Figure 9:
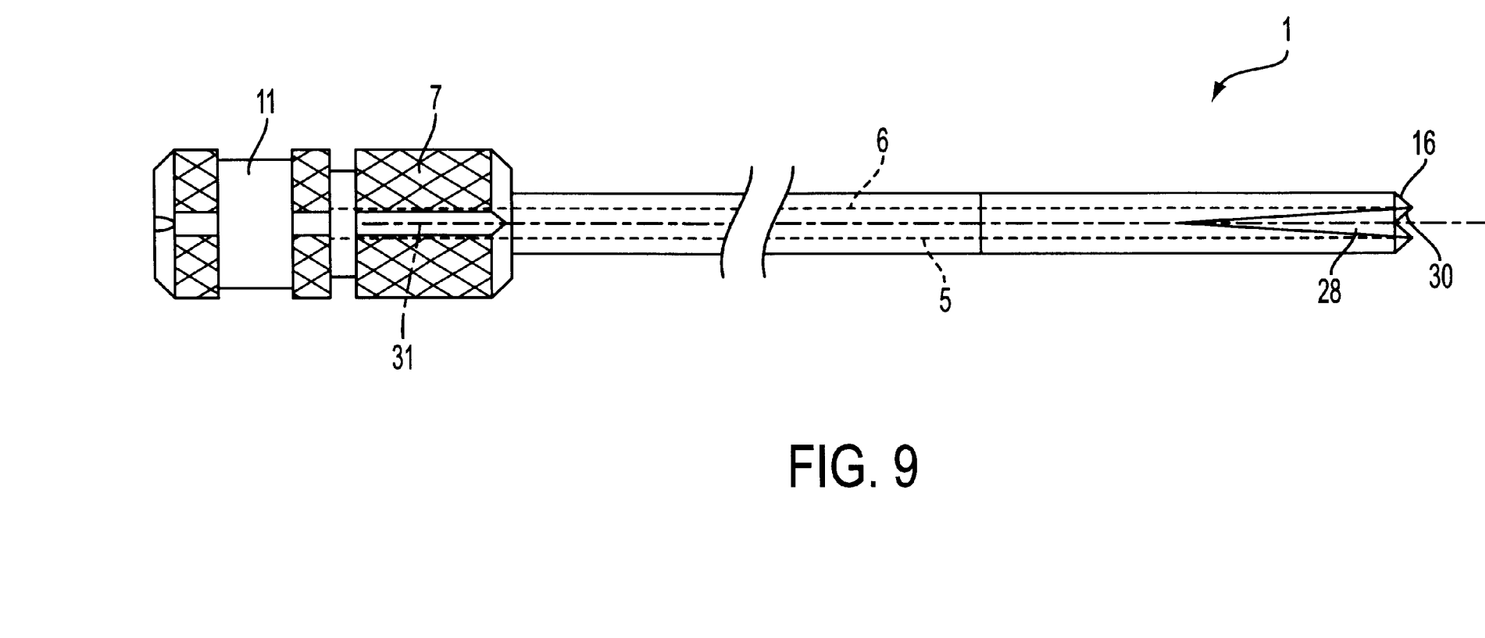
FIGS. 9 to 11 are views depicting an alternative form of the applicator allowing it to be used as a knot pusher.
Figure 10:
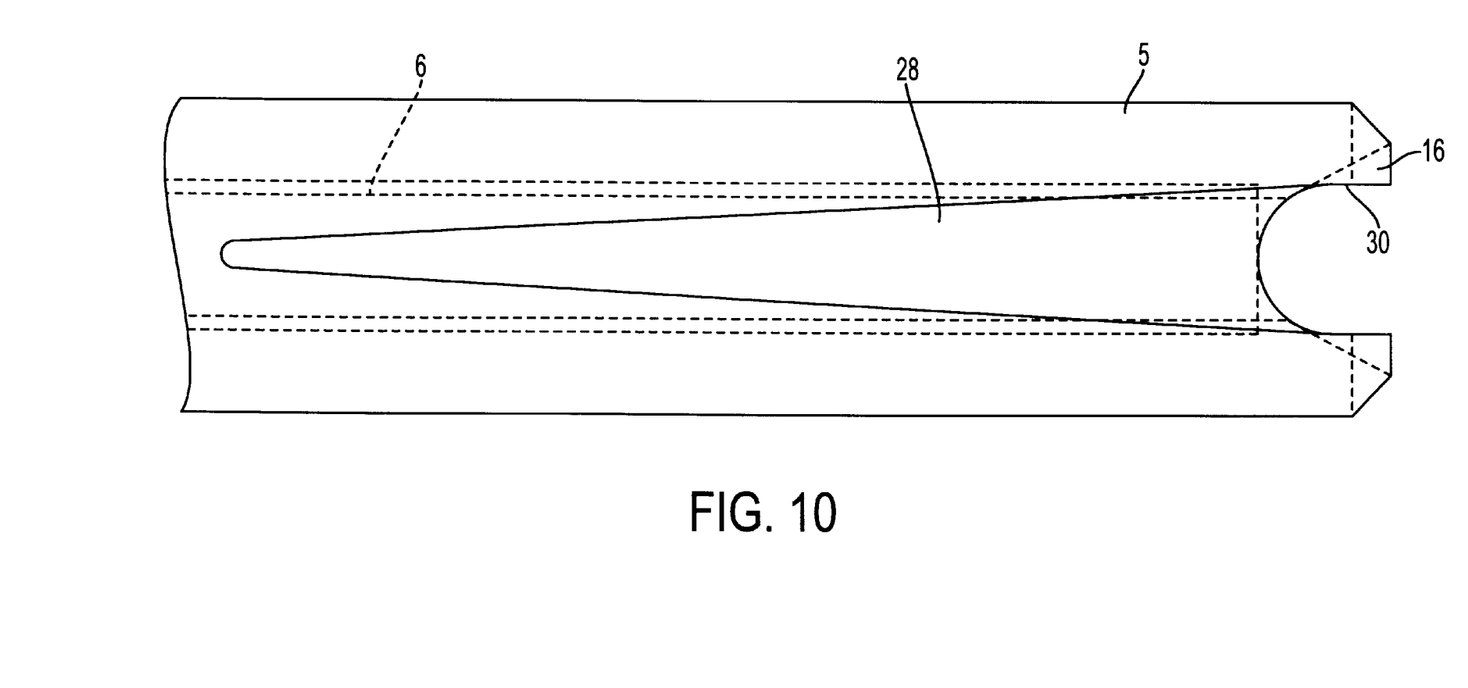
Figure 11:
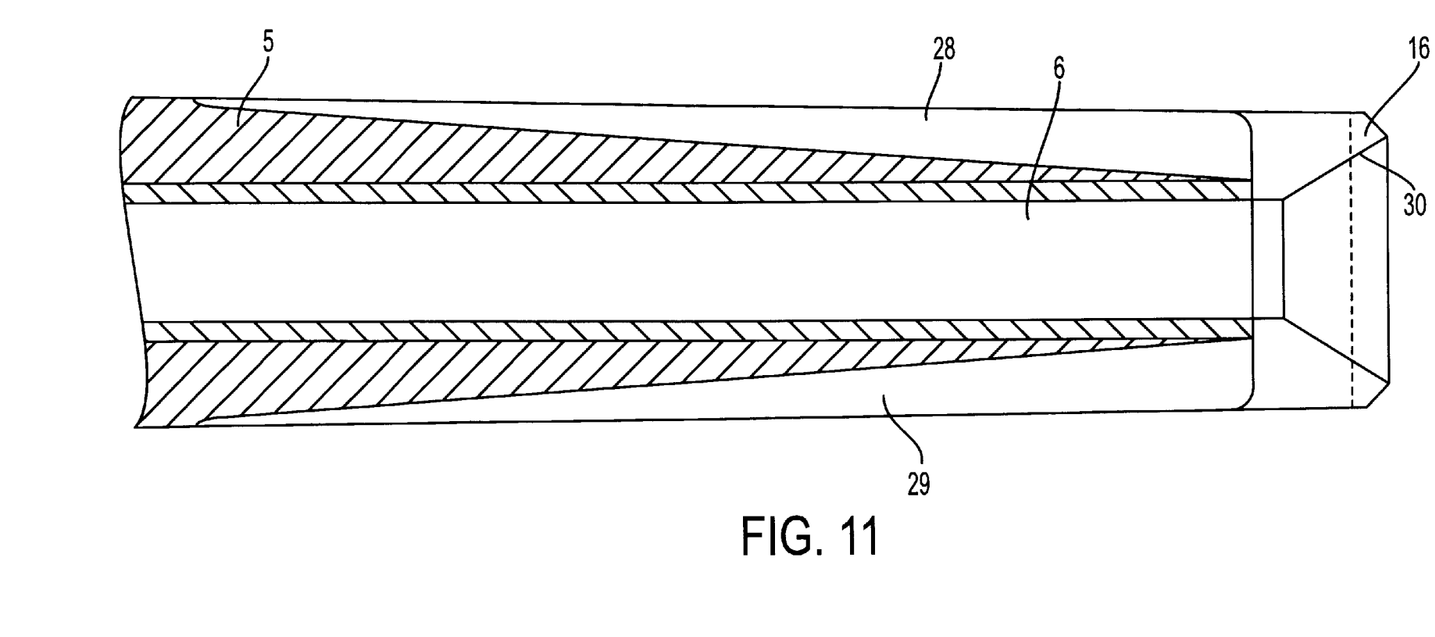

FIGS. 9 to 11 show an alternative form of the applicator 1, and more particularly of the sleeve 5, which, at its free end 16, which is the opposite end to the head 7, has a mechanism for guiding the suture thread 9 when the knots are tied outside the human body, or are extra-corporal knots.

Starting from the end 16 and working toward the head 7, the sleeve 5 has two channels 28 and 29 which are diametrically opposed and parallel to the longitudinal axis of the applicator 1.

Each channel 28 and 29 has a V-shaped profile, the most open or widest end of which faces toward the end 16. Also, each channel 28 and 29 has a depth which decreases along the periphery of the sleeve 5 so that the deepest point is at the free end 16 and the most open end of the V.

The end 16 of the sleeve 5 has a slit 30 arranged at right angles to the channels 28, 29 so that each channel collaborates with the slit 30. The diameter of the slit 30 is approximately identical to the dimensions of the most open end of the V forming the profile of each channel 28, 29. The slit 30 forms a hollow inside the sleeve 5, which communicates with the internal bore 6 in which the rod 13 and the needle 2 secured to the suture thread 9 slide.

Finally, in line with the channels 28, 29, respectively, the head 7 of the sleeve 5 has a recess 31 which gives the surgeon a reference for positioning the slit 30 and the channels at the operating site.

What happens is that the sleeve 5 with the channels 28, 29, the slit 30 and the recesses 31 allows the surgeon to make knots in the suture thread 9 outside the human body. The sleeve 5 allows the surgeon to place the knot in the slit 31, while each end of the suture thread 9 is placed in the channels 28 and 29 of the sleeve 5.

The surgeon introduces the sleeve 5 into the trocar 3, holding the ends of the suture thread 9 one on each side of the sleeve 5, so as to push the knot held in the slit 31 into the trocar and make it slide along the latter to bring it to the operating site and ligature the wound.

What is claimed is:

1. An applicator for setting a needle secured to a suture thread, the applicator comprising:
   an elongated sleeve comprising a bore, a first end and a second end, the needle being disposed within the bore near the second end;
   a rod having a first end and a second end, the second end being adapted to slide within the bore and rest adjacent the needle; and
   a retaining mechanism for maintaining the position of the rod with respect to the elongated sleeve.

2. The applicator of claim 1, wherein the second end of the rod rests against the needle.

3. The applicator of claim 1, wherein needle can exit the bore from the second end of the elongated sleeve when the second end of the rod is moved into contact with the needle.

4. The applicator of claim 1, wherein the first end of the elongated sleeve comprises a tensioning mechanism disposed within the bore.

5. The applicator of claim 4, wherein the tensioning mechanism traps the suture thread between an inside surface of the bore and an outside surface of the tensioning mechanism.

6. The applicator of claim 5, wherein the first end of the elongated tube comprises an internal housing and wherein the tensioning mechanism comprises a flexible ring, the flexible ring being disposed within the internal housing.

7. The applicator of claim 1, wherein the retaining mechanism comprises a plate having at least a first and second gripper, the first gripper being adapted to retain the first end of the rod and the second gripper being adapted to retain the first end of the elongated sleeve.

8. The applicator of claim 7, wherein the plate comprises an oblong shape.

9. The applicator of claim 1, wherein the first end of the elongated sleeve comprises a cylindrical head portion which is larger than the second end of the elongated sleeve.

10. The applicator of claim 9, wherein the cylindrical head portion comprises a recess which is engageable with a gripper of the retaining mechanism.

11. The applicator of claim 1, wherein the first end of the rod comprises a stop portion which is larger than the second end of the rod.

12. The applicator of claim 11, wherein the stop portion comprises a recess which is engageable with a gripper of the retaining mechanism.

13. The applicator of claim 1, wherein the first end of the elongated sleeve comprises a cylindrical head portion which is larger than the second end of the elongated sleeve, the cylindrical head portion comprising a recess which is engageable with a second gripper of the retaining mechanism and wherein the first end of the rod comprises a stop portion which is larger than the second end of the rod, the stop portion comprising a recess which is engageable with a first gripper of the retaining mechanism.

14. The applicator of claim 13, wherein a distance between the first and second grippers corresponds to a distance which is less than a length of the needle disposed within the bore so that the needle is set back some distance from the second end of the elongated sleeve.

15. The applicator of claim 1, wherein retaining mechanism comprises a through hole for allowing the suture thread to pass therethrough.

16. The applicator of claim 15, wherein the through hole is centrally disposed on a plate of the retaining mechanism.

17. The applicator of claim 15, wherein the through hole cooperates with a slit which opens to a peripheral groove formed on a plate of the retaining mechanism.

18. The applicator of claim 17, wherein the peripheral groove formed on the plate comprises an area for retaining a portion of the suture thread which is wrapped therein.

19. The applicator of claim 1, wherein the second end of the rod comprises a hook shaped notch.

20. The applicator of claim 19, wherein the hook shaped notch is oriented at an angle of 30 degrees relative to a center axis of the bore.

21. The applicator of claim 19, wherein the hook shaped notch extends less than half way across a diameter of the second end of the rod.

22. The applicator of claim 1, wherein the second end of the elongated sleeve comprises at least one channel which is parallel to an axis of the bore and a slit which is perpendicular to the at least one channel.

23. The applicator of claim 22, wherein the at least one channel comprises two channels which are diametrically opposed.

24. The applicator of claim 23, wherein each channel comprises a v-shaped profile so that each channel is wider near the second end and narrower near the first end of the elongated sleeve.

25. The applicator of claim 24, wherein each channel extends deeper into a side wall of the second end than a depth near the first end of the elongated sleeve.

26. The applicator of claim 24, wherein the slit comprises a rounded profile whose diameter substantially corresponds to a width of at least one channel near the second end of the elongated sleeve.

27. The applicator of claim 22, wherein the slit extends across the bore at the second end of the elongated sleeve.

28. The applicator of claim 22, wherein the first end of the elongated sleeve comprises a recess which is oriented to the at least one channel.

29. An applicator for setting a needle secured to a suture thread, the applicator comprising:
   an elongated sleeve comprising a handle, a free end and a bore extending from the handle to the free end, the needle being disposed within the bore near the free end;
   a rod comprising a handle and a free end, the free end being adapted to slide within the bore so as to rest adjacent the needle; and
   a retaining mechanism for maintaining the position of the rod with respect to the elongated sleeve, the retaining mechanism comprising a plate, a first gripper and a second gripper,
   wherein the first gripper releasably secures the handle of the rod and wherein the second gripper releasably secures the handle of the elongated sleeve.

30. A method of assembling an applicator for setting a needle secured to a suture thread, the applicator comprising an elongated sleeve comprising a bore, a first end and a second end, the needle being disposed within the bore near the second end, a rod having a first end and a second end, the second end being adapted to slide within the bore and rest adjacent the needle, and a retaining mechanism for maintaining the position of the rod with respect to the elongated sleeve, the method comprising:
   securing the suture thread to the needle;
   placing the needle and a portion of the thread into the bore of the elongated sleeve;

introducing the second end of the rod into the bore until it is positioned adjacent the needle;

retaining the first end of the rod on the retaining mechanism; and retaining the first end of the elongated sleeve on the retaining mechanism.

31. A method of using an applicator for setting a needle secured to a suture thread, the applicator comprising an elongated sleeve comprising a bore, a first end and a second end, the needle being disposed within the bore near the second end, a rod having a first end and a second end, the second end being adapted to slide within the bore and rest adjacent the needle, and a retaining mechanism for maintaining the position of the rod with respect to the elongated sleeve, the method comprising:

releasing the first end of the rod from the retaining mechanism;

releasing the first end of the elongated sleeve from the retaining mechanism; and moving the first end of the rod towards the first end of the elongated sleeve, wherein the second end of the rod forces the needle out of the second end of the elongated sleeve when the rod is moved.

* * * * *